(12) United States Patent (10) Patent No.: US 8,097,278 B2
Sackler (45) Date of Patent: Jan. 17, 2012

(54) COMPARTMENTALIZED DOSAGE FORM

(75) Inventor: Richard S. Sackler, Greenwich, CT (US)

(73) Assignee: Purdue Pharma L. P., Stamford, CT (US)

( * ) Notice: Subject to any disclaimer, the term of this patent is extended or adjusted under 35 U.S.C. 154(b) by 0 days.

(21) Appl. No.: 11/533,391

(22) Filed: Sep. 20, 2006

(65) Prior Publication Data

US 2007/0026068 A1 Feb. 1, 2007

Related U.S. Application Data

(63) Continuation of application No. 10/477,383, filed as application No. PCT/US02/16268 on May 22, 2002, now Pat. No. 7,125,561.

(60) Provisional application No. 60/292,598, filed on May 22, 2001.

(51) Int. Cl.
*A61K 9/48* (2006.01)
(52) U.S. Cl. ........ 424/451; 424/453; 424/454; 424/463; 424/464
(58) Field of Classification Search .................. None
See application file for complete search history.

(56) References Cited

U.S. PATENT DOCUMENTS

| 5,137,733 | A | * | 8/1992 | Noda et al. ..................... 424/497 |
| 5,866,164 | A | | 2/1999 | Kuczynski et al. |
| 6,228,863 | B1 | | 5/2001 | Palermo et al. |
| 6,277,384 | B1 | | 8/2001 | Kaiko et al. |
| 6,865,444 | B2 | | 3/2005 | Howard ........................ 700/237 |
| 2003/0004177 | A1 | * | 1/2003 | Kao et al. ...................... 514/282 |
| 2004/0146547 | A1 | * | 7/2004 | Marcenyac et al. ........... 424/449 |
| 2004/0241218 | A1 | | 12/2004 | Tavares et al. ................. 424/449 |
| 2005/0163856 | A1 | | 7/2005 | Maloney et al. .............. 424/486 |

OTHER PUBLICATIONS

Derwent abstract No. DE 2133122 A, Jul. 22, 1976, Daiichi Seiyaku Co., "Multi-Layer Tablets with Controlled Stopwise Release."

* cited by examiner

*Primary Examiner* — Susan Tran
(74) *Attorney, Agent, or Firm* — McDermott Will & Emery LLP

(57) ABSTRACT

The present invention provides a dosage form that prevents misuse of the medicament contained within. The dosage form contains an inactivating substance in combination with the medicament, wherein the two substances are separated by a permeable or semi-permeable partition. The partition becomes impermeable upon activation by a medical professional, thereby effectively sequestering the inactivating substance from the medicament and allowing for the intended administration of the medicament to the patient. Unless activated, however, the inactivating substance and medicament remain commingled in the dosage form, and any attempt to dispense the medicament before activation will result in the release of inactivated medicament.

2 Claims, 1 Drawing Sheet

COMPARTMENTALIZED DOSAGE FORM

CROSS REFERENCE TO RELATED APPLICATIONS

Reference is made to U.S. application Ser. No. 60/292,598, filed May 22, 2001, which is incorporated herein by reference.

FIELD OF THE INVENTION

This invention relates to a dosage form that prevents misuse of the medicament contained within. The dosage form includes an inactivating substance in combination with the medicament, wherein the two substances are separated by a permeable or semi-permeable partition. The partition becomes impermeable upon activation by a pharmacist or other medical professional, thereby effectively sequestering the inactivating substance from the medicament. However, unless activated, the inactivating substance and medicament remain commingled in the dosage form, and any attempt to dispense the medicament before activation will result in the release of inactivated medicament.

BACKGROUND OF THE INVENTION

Approximately 90% of all drugs used to produce a systemic effect are administered via the oral route. Of those administered orally, tablets are preferred for a variety of reasons. For example, tablets are unit dose forms that offer the greatest uniformity of content, in a light and compact package. In addition, tablets are relatively simple and inexpensive to produce, package, and ship. Tablets also offer the greatest ease of swallowing, especially when coated, they easily lend themselves to certain special-release profile products, such as enteric or delayed-release products, and they have the best combined properties of chemical, mechanical, and microbiological stability of all oral dosage forms. For at least these reasons, a wide variety of medications are currently available in tablet form. However, oral dosage forms are not free from abuse, especially certain analgesics that are capable of rapid pain relief with a simultaneous euphoric effect.

Enteric coatings have been used to modify drug release in oral dosage forms. Enteric coatings are designed to remain intact in the stomach, but will dissolve and release the contents of the dosage form in the small intestine. The coatings are generally used to delay the release of drugs that are inactivated by the stomach contents or that may irritate the gastric mucosa, thereby causing nausea or bleeding. The action of enteric coatings results from a difference in composition of the gastric and intestinal environments with respect to pH and the presence of endogenous enzymes. Most enteric coatings are formulated to remain intact in the low pH of the stomach, but readily dissolve when the pH rises to about 4-5. The most effective enteric polymers are poly acids having a pKa of 3-5. See *Remington: The Science and Practice of Pharmacy* 19$^{th}$ Ed., Ed. Alfonso R. Gennaro, et al., Philadelphia College of Pharmacy and Science (1995), p. 1653 et seq. However, enteric coatings have not been used to deter abuse and provide a tamper resistant dosage form.

U.S. Pat. No. 5,507,277 to Rubsamen, et al., relates to a method of controlling access to a drug that is administered by an intrapulmonary delivery device having an electronic lock and key mechanism. Access to the drug in the device is limited to the intended user by providing that user with a uniquely coded, machine readable key that matches the code on the device lock. Contacting the lock and key signals a controlling means within the device to permit use of the device. However, Rubsamen does not address the unique problems posed by abuse of oral dosage forms.

Therefore, a need exists for an oral dosage form that delivers medication when taken as directed, but when abused, the normal delivery mechanism is circumvented or interrupted to prevent abuse by an unintended user.

SUMMARY OF THE INVENTION

Thus, it is an object of the present invention to provide a dosage form that prevents misuse of the medicament contained within. The dosage form contains an inactivating substance in combination with the medicament, wherein the two substances are separated by a permeable or semi-permeable partition. The partition becomes impermeable upon activation by a medical professional, thereby effectively sequestering the inactivating substance from the medicament and allowing for the intended administration of the medicament to the patient. Unless activated, however, the inactivating substance and medicament remain commingled in the dosage form, and any attempt to dispense the medicament before activation will result in the release of inactivated medicament.

Accordingly, it is an object of the present invention to provide a dosage form including:
(A) a first compartment comprising a medicament;
(B) a second compartment comprising an inactivating agent;
(C) a semi-permeable or permeable partition separating said first and second compartments; and
(D) an outer layer surrounding said first and second compartments, wherein said partition becomes impermeable upon exposure to a suitable stimulus, e.g., heat, electromagnetic radiation, including, but not limited to, microwaves, infra-red, visual, ultraviolet, ionizing electromagnetic radiation, and the like, thereby sequestering said medicament from said inactivating agent. The stimulus is provided by a medical professional when the dosage form is properly dispensed and administered, and without exposure to the stimulus, the contents of the first and second compartments are commingled and the medicament is inactivated.

The inactivating agent is selected from the group consisting of an indelible dye, a biological inactivating agent, a chemical inactivating agent, a denaturing inactivating agent, an electrical inactivating agent, a magnetic inactivating agent, a mechanical inactivating agent, a cross-linking inactivating agent, rat or human mu-opioid receptor, opioid neutralizing antibodies, a narcotic antagonist, irritating or dipphoric agents, or any combination thereof.

DESCRIPTION OF THE INVENTION

Figure 1:
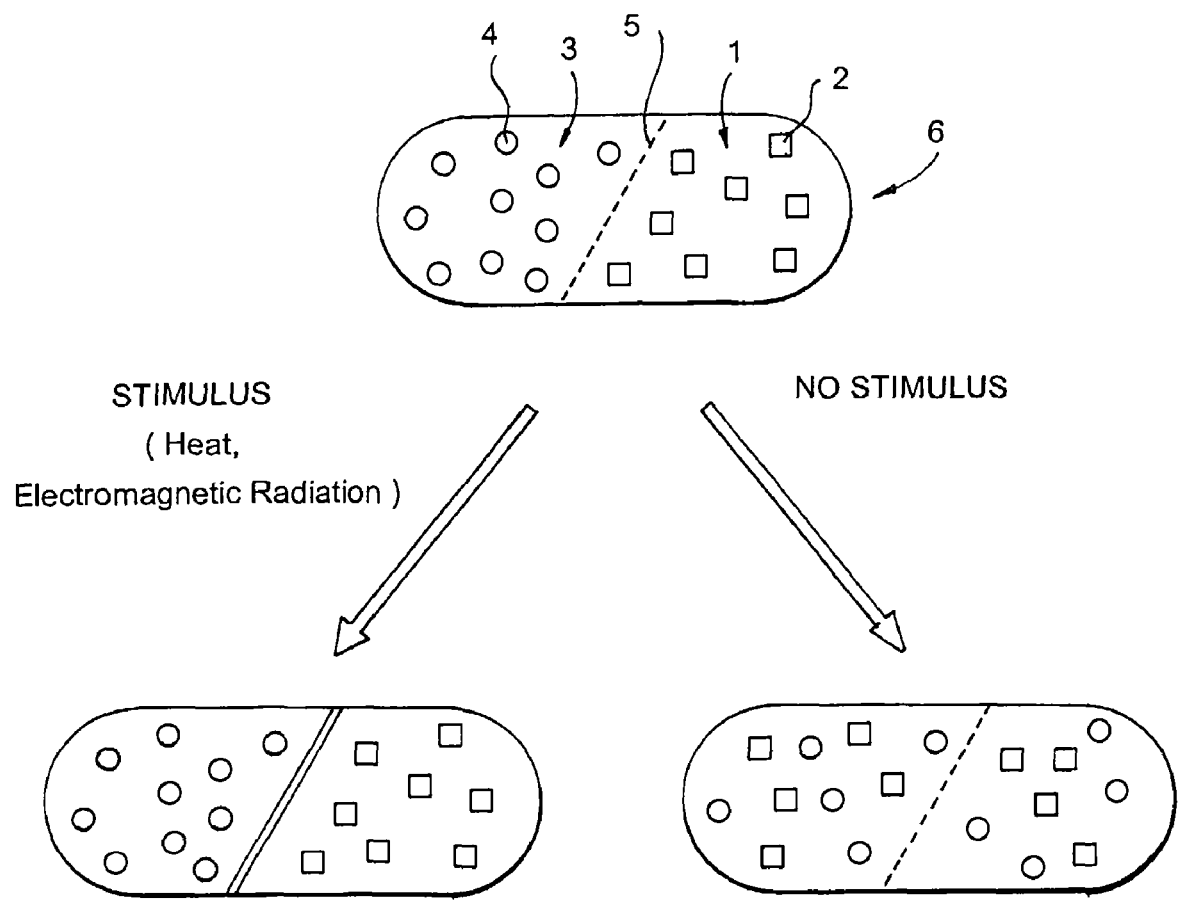
FIG. 1 shows an oral dosage form in accordance with the present invention.

As shown in FIG. 1, the oral dosage form of the present invention contains the following elements:
(A) a first compartment (1) comprising a medicament (2);
(B) a second compartment (3) comprising an inactivating agent (4);
(E) a semi-permeable or permeable partition (5) separating said first and second compartments; and
(F) an outer layer surrounding (6) said first and second compartments, wherein said partition becomes impermeable upon exposure to a suitable stimulus, e.g., heat, electromagnetic radiation, including, but not limited to, microwaves, infra-red, visual, ultraviolet, ionizing electromagnetic radiation, and the like, thereby sequestering said medicament from said inactivating agent. The stimulus is provided by a medical professional when the dosage form is properly dispensed and administered, and without exposure to the stimulus, the contents of the first and second compartments are commingled and the medicament is inactivated or ineffective for the target indication.

The inactivating agent is selected from the group consisting of an indelible dye, a biological inactivating agent, a chemical inactivating agent, a denaturing inactivating agent, an electrical inactivating agent, a magnetic inactivating agent, a mechanical inactivating agent, a cross-linking inactivating agent, rat or human mu-opioid receptor, opioid neutralizing antibodies, a narcotic antagonist, irritating or dipphoric agents, or any combination thereof.

While the dosage form may be formulated for virtually any medicament, in a preferred embodiment, the medicament is an opiate or benzodiazapene, and the inactivating agent is an opioid or benzodiazepene antagonist or a noxious agent, e.g., an emetic. In this regard, reference is made U.S. Pat. No. 4,806,341 to Chien, which discloses possible medicaments and inactivating agents that may be used in the dosage forms used in the present invention.

In practice, the dosage form is supplied to the pharmacist or other medical professional capable of dispensing pharmaceuticals with the partition in the semi-permeable or permeable form. If the pharmacist should need to dispense the dosage form to an intended patient, he will contact the dosage form with a suitable stimulus, e.g., heat, light, radiation or the like, which will render the partition within impermeable. At that time, the medicament cannot be commingled with the inactivating agent within the dosage form and the medicament will be administered properly in vivo. If, however, the stimulus is not applied to the dosage form, the partition remains permeable or semi-permeable, and the medicament and inactivating agent will be commingled by the unintended end-user. This misuse will result in the inactivation of the medicament by the inactivating agent, e.g., if the inactivating agent is a cross-linking agent it will cross-linking the medicament and render it incapable of absorption in vivo. Alternatively, the inactivation of the medicament can take the form of a competitive inhibition of the intended binding site of the medicament by the inactivating agent. For example, if the medicament is an opiate agonist, the inactivating agent can be an antagonist that will compete with the agonist for binding to the opiate receptor There are a variety of ways in which an inactivating agent can render the medicament unavailable through inactivation; for example, chemical inactivation or alteration of the receptor binding site of the medicament; electrical inactivation or alteration of the receptor binding site of the medicament; magnetic inactivation or alteration of the receptor binding site of the medicament; mechanical inactivation or alteration of the receptor binding site of the medicament; biounavailability; physical unavailability; loss of appeal of the medicament to the abuser, such as for example, an inactivating agent which creates an intolerably bad taste or an intolerable reaction such as extreme nausea or the like; or something similar thereto. One or more inactivating agent(s) may be used. Further, if the medicament were an opioid, the inactivating agent could be a chemical or denaturing agent that would alter residual opioid molecules in the dosage form and make them inactive. The inactivating agent could be an opioid receptor that would bind the residual opioid into an insoluble ligand-receptor complex. The inactivating agent could also be an opioid receptor antagonist, preferably with greater specificity and/or affinity for the receptor than the opioid, which would be isolated or delivered with the residual opioid upon misuse and compete with the residual opioid for the opioid receptor, thereby defeating the purpose of misusing the opioid. This would render the residual opioid useless in vivo. The inactivating agent could also physically sequester the medicament such as, for example, in an impermeable microsphere or in a permanently bound matrix. Similarly, the inactivating agent could be a non-opioid with distressing or dysphoric properties if absorbed that made abuse unappealing.

The dosage form may preferably contain a detection material that is also released when the dosage form is tampered with, making it visible to the user that the dosage form has been misused. The amount of detection material contained within the dosage form of the invention is that amount which, when released, will be visible to the end-user. Such amounts can easily be ascertained by the skilled artisan, based on the dimensions and permeability of the article, as well as the visibility of the detection material. Further, the amount of inactivating agent will depend upon the medicament and the amount of residual medicament that is expected in a particular dosage form. Such amounts can also be determined by those skilled in the art by methods such as establishing a matrix of amounts and effects. However, such amounts should be those amounts effective to achieve the results sought, i.e., inactivation of the residual medicament or the rendering undesirable of a therapeutic drug of abuse.

Non-limiting examples of medicaments that may be used in the present invention are fentanyl, buprenorphine, etorphine and related opioids of sufficient potency to allow transdermal usage, or any combinations thereof. Non-limiting examples of inactivating agents include the rat or human mu-opioid receptor; opioid-neutralizing antibodies; narcotic antagonists such as naloxone, naltrexne and nalmefene; dysphoric or irritating agents such as scopolamine, ketamine, atropine or mustard oils; or any combinations thereof.

The present invention may be formulated into a pharmaceutical composition. The pharmaceutical composition also may include additives, such as a pharmaceutically acceptable carrier, a flavorant, a sweetener, a preservative, a dye, a binder, a suspending agent, a dispersing agent, a colorant, a disintegrant, an excipient, a diluent, a lubricant, a plasticizer, an edible oil or any combination of any of the foregoing.

Suitable pharmaceutically acceptable carriers include, but are not limited to, ethanol; water; glycerol; aloe vera gel; allantoin; glycerin; vitamin A and E oils; mineral oil; PPG2 myristyl propionate; vegetable oils and solketal. Suitable binders include, but are not limited to, starch; gelatin; natural sugars, such as glucose, sucrose and lactose; corn sweeteners; natural and synthetic gums, such as acacia, tragacanth, vegetable gum, and sodium alginate; carboxymethylcellulose; polyethylene glycol; waxes; and the like. Suitable disintegrators include, but are not limited to, starch such as corn starch, methyl cellulose, agar, bentonite, xanthan gum and the like. Suitable lubricants include, but are not limited to, sodium oleate, sodium stearate, magnesium stearate, sodium benzoate, sodium acetate, sodium chloride and the like. A suitable suspending agent is, but is not limited to, bentoite. Suitable dispersing and suspending agents include, but are not limited to, synthetic and natural gums, such as vegetable gum, tragacanth, acacia, alginate, dextran, sodium carboxymethylcellulose, methylcellulose, polyvinyl-pyrrolidone and gelatin. Suitable edible oils include, but are not limited to, cottonseed oil, sesame oil, coconut oil and peanut oil. A suitable pharmaceutical diluent is, but is not limited to, water. Examples of additional additives include, but are not limited to, sorbitol; talc; stearic acid; and dicalcium phosphate.

The pharmaceutical compositions may be formulated as solid unit dosage forms, such as tablets, pills, and capsules. Unit dosage forms may be used for oral, sublingual, or buccal administration. Solid unit dosage forms may be prepared by mixing the compounds with a pharmaceutically acceptable carrier and any other desired additives as described above. The mixture is typically mixed until a homogeneous mixture of the compounds and the carrier and any other desired additives is formed, i.e., until the compounds are dispersed evenly throughout the composition.

Tablets or pills can be coated or otherwise compounded to form a unit dosage form that has delayed and/or prolonged action, such as time release and sustained release unit dosage forms. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. In this embodiment, the inner dosage form is a dosage form in accordance with the present invention.

The partition is semi-permeable or permeable before activation by the medical professional and upon activation, becomes impermeable. Such a partition can be prepared from, for example, NTX is inert and upon exposure to microwaves, it becomes insoluble and impermeable.

The pharmaceutical composition or unit dosage forms of the present invention may be administered by a variety of routes such as oral, buccal, and sublingual. The pharmaceutical compositions or unit dosage forms of the present invention may be administered to an animal, preferably a human being.

The daily dosage of the compounds may vary according to a variety of factors such as underlying disease states, the individual's condition, weight, sex and age and the mode of administration. For oral administration, the pharmaceutical compositions can be provided in the form of scored or unscored solid unit dosage forms containing 0.01, 0.05, 0.1, 0.5, 1.0, 2.5, 5.0, 10.0, 15.0, 25.0, or 50.0 milligrams of the agonist and/or antagonist for the symptomatic adjustment of the dosage to the patient to be treated.

The dosage regimen utilizing the formulation of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the absorption, distribution, metabolism, and excretion of a drug.

The pharmaceutical composition or unit dosage form may be administered in a single daily dose, or the total daily dosage may be administered in divided doses of two, three or four times daily. In addition, co-administration or sequential administration of other active agents may be desirable. For combination treatment with more than one active agent, where the active agents are in separate dosage formulations, the active agents can be administered concurrently, or they each can be administered at separately staggered times. The dosage amount may be adjusted when combined with other active agents as described above to achieve desired effects. On the other hand, unit dosage forms of these various active agents may be independently optimized and combined to achieve a synergistic result wherein the pathology is reduced more than it would be if either active agent were used alone.

The formulation also may be administered as an additive to the feed by simply mixing the formulation with the feedstuff or by applying the formulation to the surface of animal feed. Alternatively, the formulation may be mixed with a carrier and the resulting composition may then either be mixed with the feed or fed directly to the animal. Suitable carriers include, but are not limited to, corn meal, citrus meal, fermentation residues, soya grits, dried grains, and the like. The formulation may be intimately mixed with the carrier by any method known by those skilled in the art, including, without limitation, grinding, stirring, milling, or tumbling.

Several methods may be used to produce the unit dosage forms and formulations of the present invention. In a specific embodiment, the amount of medicament present in the formulation is a therapeutic effective amount, i.e., that amount needed to produce a health benefit in the patient to which it is administered. Any method known to one of ordinary skill in the art may be used to prepare the formulations of the invention. In a specific embodiment, melt extrusion granulation or melt extrusion method are used to produce the dosage forms of the present invention.

In addition, the present invention may also be used to prepare a transdermal dosage form.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, applications, publications, test methods, literature, and other materials cited herein are hereby incorporated by reference.

I claim:

1. An oral dosage form comprising:
   (a) a first compartment comprising a medicament;
   (b) a second compartment comprising an inactivating agent;
   (c) a semi-permeable or permeable partition comprising a hexene film resin separating said first and second compartments;
   (d) an outer layer surrounding said first and second compartments; and
   (e) a third compartment comprising a detection material which is released when the dosage form is crushed or dissolved;
   wherein said partition is capable of being rendered impermeable upon exposure to a stimulus selected from the group consisting of heat, microwave radiation, infra-red radiation, visual radiation, ultraviolet radiation, and ionizing electromagnetic radiation, such that said partition that is rendered impermeable sequesters said medicament from said inactivating agent in the oral dosage form;
   wherein the detection material becomes visible upon being released when the dosage form is crushed or dissolved; and wherein said inactivating agent is selected from the group consisting of an indelible dye, a biological inactivating agent, a chemical inactivating agent, a denaturing inactivating agent, an electrical inactivating agent, a magnetic inactivating agent, a mechanical inactivating agent, a cross-linking agent, rat or human mu-opioid receptor, opioid neutralizing antibodies, a narcotic antagonist, irritating or dipphoric agents, an emetic, and a combination thereof.

2. A dosage form of claim 1 wherein said medicament is an opiate or benzodiazepine and the inactivating agent is selected from the group consisting of an opioid or benzodiazepine antagonist and an emetic.

\* \* \* \* \*